US009205445B2

(12) United States Patent
Fang et al.

(10) Patent No.: US 9,205,445 B2
(45) Date of Patent: Dec. 8, 2015

(54) ROTARY NEBULIZATION DEVICE

(71) Applicant: MICRO BASE TECHNOLOGY CORPORATION, Bade, Taoyuan County (TW)

(72) Inventors: Tun-Ying Fang, Bade (TW); Tai-Shuan Lin, Bade (TW); Chia-Lun Hsieh, Bade (TW); Shao-Ming Yang, Bade (TW); Yu-De Su, Bade (TW); Chi-Shan Hung, Bade (TW)

(73) Assignee: Micro Base Technology Corporation, Bade, Taoyuan County (TW)

( * ) Notice: Subject to any disclaimer, the term of this patent is extended or adjusted under 35 U.S.C. 154(b) by 310 days.

(21) Appl. No.: 13/845,098

(22) Filed: Mar. 18, 2013

(65) Prior Publication Data

US 2014/0175190 A1 Jun. 26, 2014

(30) Foreign Application Priority Data

Dec. 21, 2012 (TW) ............................ 101224794 A

(51) Int. Cl.

| | |
|---|---|
| ***B05B 17/06*** | (2006.01) |
| ***A61M 11/00*** | (2006.01) |
| ***B05B 1/28*** | (2006.01) |
| *B05B 15/10* | (2006.01) |

(52) U.S. Cl.

CPC ............ *B05B 17/0607* (2013.01); *A61M 11/00* (2013.01); *B05B 1/28* (2013.01); *A61M 2205/276* (2013.01); *B05B 15/10* (2013.01)

(58) Field of Classification Search

CPC ............ B05B 1/08; B05B 3/04; A61M 11/02
USPC ............ 128/200.14, 200.23; 239/370, 102.1, 239/102.2, 338, 337, 390, 436; 222/153.13, 222/153.14, 502, 548
See application file for complete search history.

(56) References Cited

U.S. PATENT DOCUMENTS

| | | | | |
|---|---|---|---|---|
| 5,533,510 | A * | 7/1996 | Koch, III ............ | A61B 8/0883 600/443 |
| 5,964,416 | A * | 10/1999 | Jaeger .............. | A61M 15/0065 222/383.1 |
| 7,458,486 | B2 * | 12/2008 | Weist et al. .................... | 222/83 |
| 2007/0227816 | A1 * | 10/2007 | Uejima ................ | F16F 1/3737 181/294 |
| 2010/0222752 | A1 * | 9/2010 | Collins, Jr. .......... | A61M 11/042 604/296 |
| 2011/0101023 | A1 * | 5/2011 | Chan et al. ........................ | 222/1 |
| 2013/0112771 | A1 * | 5/2013 | Ki et al. ..................... | 239/102.2 |

FOREIGN PATENT DOCUMENTS

| | | | |
|---|---|---|---|
| TW | 101224273 | * 12/2012 | ............. B05B 17/00 |

* cited by examiner

*Primary Examiner* — Arthur O Hall
*Assistant Examiner* — Christopher R Dandridge
(74) *Attorney, Agent, or Firm* — Leong C. Lei

(57) ABSTRACT

Disclosed is a rotary nebulization device installed to a container that contains a liquid to be nebulized, and the rotary nebulization device includes a main body, an electric connection ring, an nebulization ring and a rotary ring. The main body contains a power supply, the electric connection ring, the nebulization ring and the rotary ring sequentially installed on a side of the main body, and the electric connection ring has a first contact electrically coupled to the power supply, and the nebulization ring has an nebulization module electrically coupled to the first contact, and the rotary ring has a second contact corresponding to the first contact. The corresponding container has an opening portion and a liquid storage slot, and the rotary ring is provided for switching the connection and electric conduction between the liquid storage slot and the nebulization module to improve the convenience of operation.

17 Claims, 6 Drawing Sheets

ROTARY NEBULIZATION DEVICE

CROSS-REFERENCE TO RELATED APPLICATIONS

This non-provisional application claims priority under 35 U.S.C. §119(a) on Patent Application No(s). 101224794 filed in Taiwan, R.O.C. on Dec. 21, 2012, the entire contents of which are hereby incorporated by reference.

BACKGROUND OF THE INVENTION

1. Field of the Invention

The present invention relates to the field of liquid nebulization devices, and more particularly to a rotary nebulization device that switches the supply of a liquid to be nebulized and operates a power supply of the rotary nebulization device by a rotating method.

2. Description of the Related Art

In recent years, various different kinds of nebulization devices are used extensively in the areas of medical healthcare and cosmetics. For example, a liquid such as the medicine or cosmetic solution is nebulized to form gas molecules which are used for maintaining or curing respiratory tract, improving human immunity, softening pores for easy removal of dead skin cells and dirt, and supplementing water quickly to maintain skin smooth, clean and exquisite.

The operation principle of the nebulization devices is to generate vibration energy by a piezoelectric device, and then transmit the vibration energy to a spray orifice plate through a conduction plate to nebulize a liquid passing through the spray orifice plate and spray the nebulized liquid to the outside. Therefore, the liquid including the medicine and cosmetic solutions can be nebulized to form small gaseous molecules that can be absorbed by human body easily. Particularly, it is necessary to control the consumption of a medicine for a specific medical treatment effectively and avoid overdose and underdose that may affect the efficacy of the medical treatment.

To facilitate users to carry and operate the nebulization device, a vast majority of the present nebulization devices are designed with a small volume, and the most common design is in a circular cylindrical shape or a lipstick-like shape and includes a liquid storage space, an nebulization module and a power supply therein, and the liquid to be nebulized is filled into the liquid storage space, and the built-in power supply is provided for driving the nebulization module to release, nebulize and spray the liquid, so that users can carry the device with them and operate the device anytime, anywhere. Since the liquid to be nebulized flows into the liquid storage space gradually by the gravity, therefore there is still a portion of the liquid overflowing or permeating to the outside from the nebulization module after use, and thus not only contaminating the nebulization device, but also contaminating other objects around the nebulization device. Therefore, most nebulization devices available in the market come with a slide bracket covered onto the front side of the nebulization module to avoid the overflow of the liquid to be nebulized when the nebulization device is not in use.

However, the switches of the slide bracket and the nebulization device are installed separately, so that two steps are required for the operation and cause inconvenience to users. Furthermore, the liquid to be nebulized must be packaged into a container in advance to facilitate a direct installation of the container into the liquid storage space. During use, the container is rotated and combined with the nebulization device or operated in an operation habit contrary to the original design of the slide bracket, so that the problem of unsmooth operations often occurs. Obviously, the conventional nebulization device requires improvements.

SUMMARY OF THE INVENTION

In view of the problems of the prior art, it is a primary objective of the present invention to provide a rotary nebulization device having an electric connection ring, an nebulization ring and a rotary ring. After the rotary ring is rotated with respect to the electric connection ring and the nebulization ring, a liquid to be nebulized can be interconnected with the nebulization ring and electrically drives the nebulization ring to release, nebulize and spray the liquid to be nebulized, characterized in that a rotation method is used to carry out the operation that fits a user's operation habit and improves the convenience of use.

Another objective of the present invention is to provide a rotary nebulization device having a safety ring for temporarily locking the rotary ring to avoid the overflow caused by an erroneous operation, so as to improve the practicability and the convenience of use of the nebulization device.

To achieve the aforementioned objectives, the present invention provides a rotary nebulization device installed to a container that contains a liquid to be nebulized and has a seal film covered onto an opening of the container, comprising: a main body, having a containing space formed therein and provided for installing a power supply; an electric connection ring, fixed onto a side of the main body and electrically coupled to the power supply, and the electric connection ring having a pair of first contacts disposed thereon; an nebulization ring, fixed to a side of the electric connection ring, and having an nebulization module interconnected to the outside and electrically coupled to the first contact; and a rotary ring, movably mounted onto the nebulization ring, and having a second contact corresponding to the electric connection ring, and an opening portion and a liquid storage slot corresponding to the container, and the opening portion having a film breaking structure corresponding to the seal film, such that when the container is installed to the rotary ring, the film breaking structure scratches or cuts the seal film to let the liquid to be nebulized flow into the liquid storage slot, and the liquid storage slot being normally staggered with the nebulization module to define a closed status, and after the rotary ring is turned, the liquid storage slot is aligned precisely with the nebulization module, and the second contact and the first contact are electrically conducted to define an open status that releases, nebulizes and sprays the liquid to be nebulized.

In a preferred embodiment of the present invention, the rotary nebulization device further comprises a safety ring movably sheathed on the main body, the electric connection ring, the nebulization ring and the rotary ring. In addition, the rotary ring has at least one first position-limiting portion disposed on an external wall of the rotary ring, and the electric connection ring has at least one bump disposed on an external wall of the electric connection ring, and the safety ring has a second position-limiting portion and a stop portion disposed on internal walls of the safety ring corresponding to the first position-limiting portion and the bump respectively for limiting the slide of the safety ring to a position outside the main body, the electric connection ring, the nebulization ring and the rotary ring to prevent the safety ring from falling off. When the safety ring is situated outside the rotary ring, the position-limiting portions can be used for locking the rotary ring to prevent the rotary ring from being rotated by an erroneous operation.

In addition, the rotary nebulization device of the present invention further comprises a water sealing plate installed on a side of the liquid storage slot corresponding to the internal wall of the nebulization ring and tightly coupled to the internal wall of the nebulization ring. Further, the water sealing plate has a circular protruding ring installed on a side corresponding to the nebulization module. The water sealing plate is provided to avoid the occurrence of overflow or leakage of the liquid to be nebulized.

To facilitate the assembling process and limiting the rotation angle of the rotary ring, the nebulization device of the present invention has an elastic snap-in portion disposed on a side proximate to the liquid storage slot, and the internal wall of the nebulization ring has a position-limiting arc slot corresponding to the elastic snap-in portion, and the elastic snap-in portion is movably snapped into the position-limiting arc slot, such that the rotary ring can be rotated with respect to the nebulization ring within a restricted angular range.

To facilitate the assembling process, the electric connection ring has a snap-in portion disposed on a side of the first contact, and the nebulization ring has a snap-in hole corresponding to the snap-in portion, such that the snap-in portion can be snapped into the snap-in hole for the installation.

In a preferred embodiment of the present invention, the rotary nebulization device further comprises a sealing rubber ring installed in the opening portion and disposed at the external periphery of the film breaking structure, and the sealing rubber ring is tightly coupled to an opening of the container.

Wherein, the rotary ring has an anti-slip portion disposed on an external wall of the rotary ring for increasing the friction for the operation and improving the user's operation feel to facilitate the rotation of the rotary ring.

Wherein, the nebulization ring has a first indicating portion disposed on the external wall of the nebulization ring and corresponding to the nebulization module, and the rotary ring has a second indicating portion disposed on the external wall of the rotary ring and corresponding to the first indicating portion. When the first indicating portion and the second indicating portion are aligned precisely with each other, the liquid storage slot is interconnected with the nebulization module to provide a convenient way for users to observe the operation directly.

DETAILED DESCRIPTION OF THE PREFERRED EMBODIMENTS

The technical content of the present invention will become apparent with the detailed description of preferred embodiments and the illustration of related drawings as follows.

Figure 1:
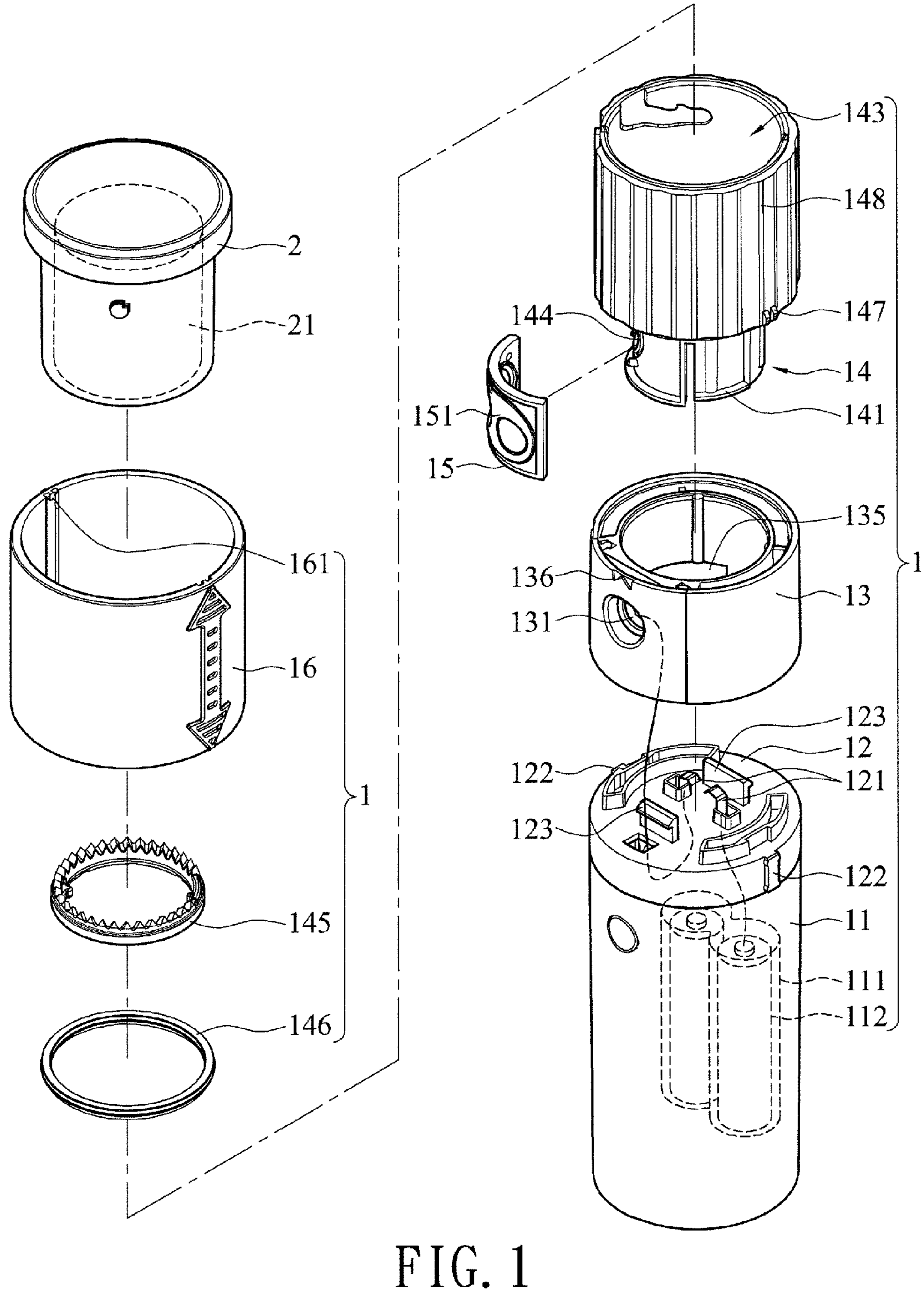
FIG. 1 is an exploded view of a rotary nebulization device of a preferred embodiment of the present invention, viewing from the top side of the device.
Figure 2:
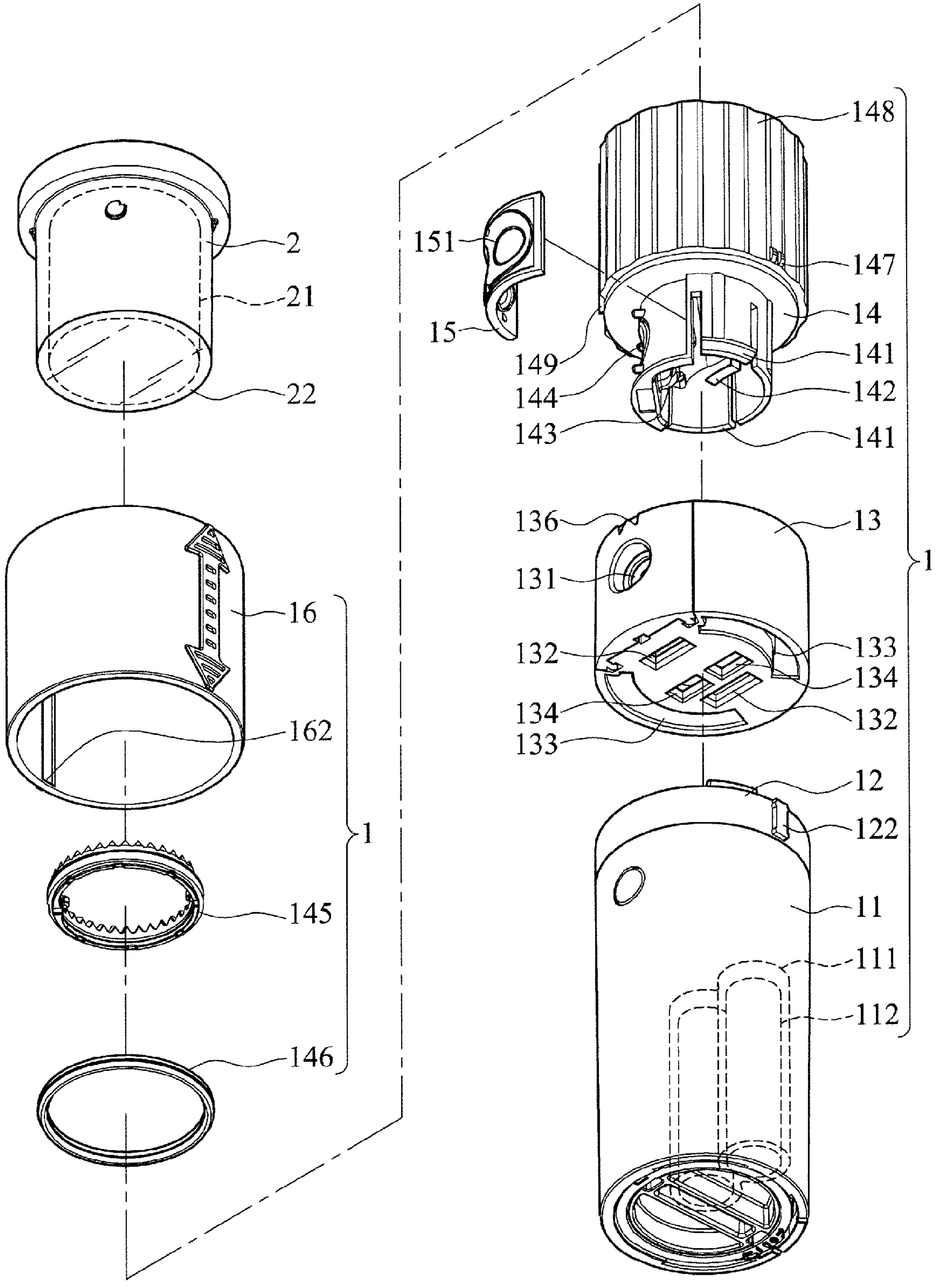
FIG. 2 is an exploded view of a rotary nebulization device of a preferred embodiment of the present invention, viewing from the bottom side of the device.
Figure 3:
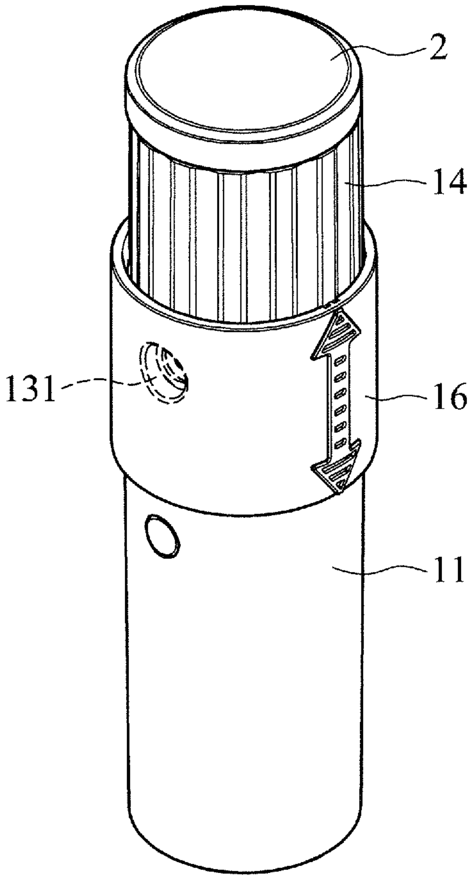
FIG. 3 is a first schematic view of a using status of a rotary nebulization device of a preferred embodiment of the present invention.
Figure 4:
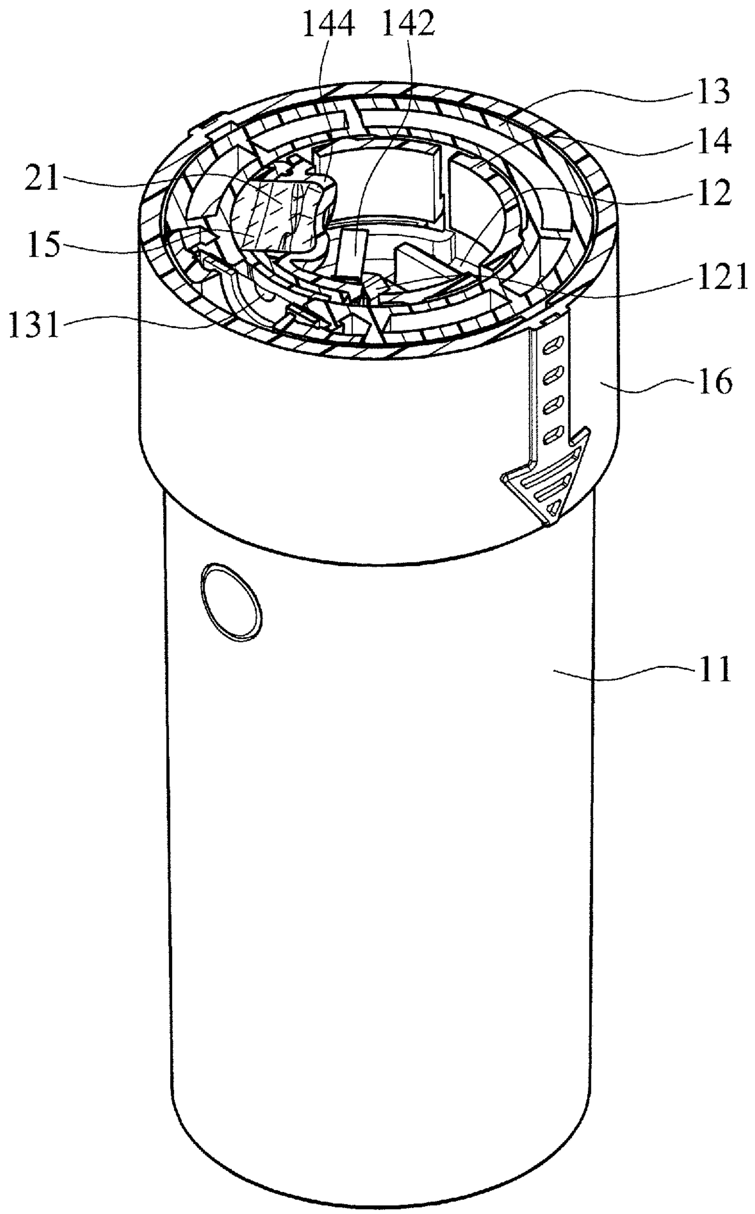
FIG. 4 is a second schematic view of a using status of a rotary nebulization device of a preferred embodiment of the present invention.
Figure 5:
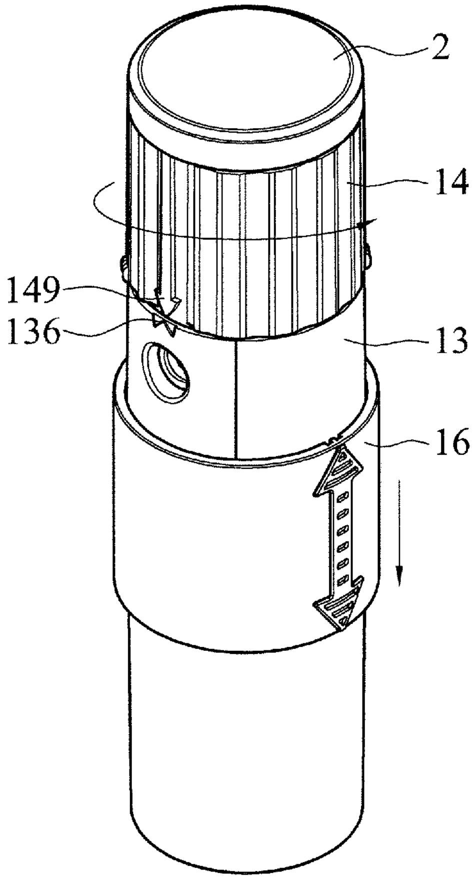
FIG. 5 is a third schematic view of a using status of a rotary nebulization device of a preferred embodiment of the present invention.
Figure 6:
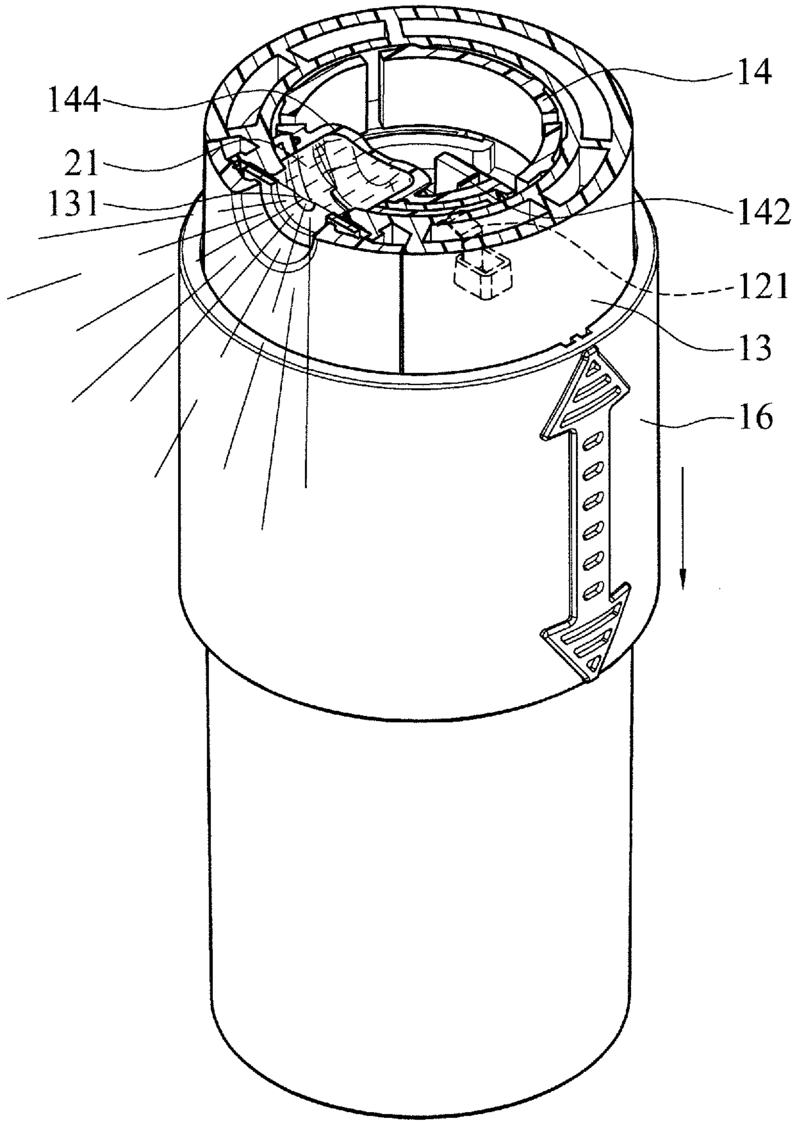
FIG. 6 is a fourth schematic view of a using status of a rotary nebulization device of a preferred embodiment of the present invention.

With reference to FIGS. 1 and 2 for the exploded views of a rotary nebulization device of a preferred embodiment of the present invention, viewing from the top side and the bottom side of the device respectively, the rotary nebulization device 1 provided for installing to a container 2 that contains a liquid to be nebulized 21 and has a seal film 22 covered onto an opening of the container 2. The rotary nebulization device 1 comprises a main body 11, an electric connection ring 12, an nebulization ring 13 and a rotary ring 14.

The main body 11 is a hollow circular cylinder having a containing space 111 formed therein and provided for installing a power supply 112. It is noteworthy that a general dry cell or a rechargeable battery is chosen as the power supply 112 to facilitate users to carry, and the power supply 112 may includes a control circuit board (not shown in the figure).

The electric connection ring 12 has an outer profile corresponding to the main body 11 to form a circular ring structure, and the electric connection ring 12 is fixed onto the top of the main body 11 and electrically coupled to the power supply 112, and the top of the electric connection ring 12 has a pair of first contacts 121, and the power supply is electrically coupled to one of the first contacts 121. In addition, a pair of bumps 122 are disposed on an external wall of the electric connection ring 12 and arranged symmetrically with each other. Further, a pair of snap-in portions 123 are disposed at the top of the electric connection ring 12 and arranged symmetrically with each other.

The nebulization ring 13 has an nebulization module 131 interconnected to the outside, and the nebulization module 131 is electrically coupled to the other first contact 121, so that the pair of first contacts 121 are normally disconnected with each other, and the bottom of the nebulization ring 13 has a pair of snap-in holes 132 corresponding to the pair of snap-in portions 123 respectively and a pair of positioning holes 133 corresponding to the pair of position-limiting arc slots respectively for positioning and fixing the nebulization ring 13 to the top of the electric connection ring 12. In addition, the nebulization ring 131 has a pair of through holes 134 formed at the bottom of the nebulization ring 131 and corresponding to the pair of first contacts 121, such that the pair of first contacts 121 can be passed through the pair of through holes 134 and exposed from the nebulization ring 13. Further, the nebulization ring 131 has a pair of position-limiting arc slots 135 formed on the internal wall of the nebulization ring 121 and at a position proximate to the electric connection ring 12, and the pair of position-limiting arc slots 135 are arranged symmetrically with each other.

The rotary ring 14 has a pair of elastic snap-in portions 141 disposed at the bottom of the rotary ring 14 and corresponding to the pair of position-limiting arc slots 135 for snapping the pair of elastic snap-in portions 141 into the pair of position-limiting arc slots 135 respectively, such that the rotary ring 14 can be latched into the nebulization ring 13 for rotation. In addition, the rotary ring 14 can be rotated with respect to the nebulization ring 13 within a restricted angular range by means of a relative relation between the pair of elastic snap-in portions 141 and the pair of position-limiting arc slots 135. Further, the rotary ring 14 has a second contact 142 corresponding to the electric connection ring 12, such that when the rotary ring 14 is rotated, the second contact 142 is in contact with the pair of first contacts 121 for an electric conduction. The rotary ring 14 has an opening portion 143 and a liquid storage slot 144 corresponding to the container 2, and the opening portion 143 has a film breaking structure 145 installed therein and corresponding to the seal film 22. In addition, the opening portion 143 has a sealing rubber ring 146 disposed at the external periphery of the film breaking structure 145, and the sealing rubber ring 146 is tightly coupled to an opening of the container 2. It is noteworthy that the rotary ring 14 has a first position-limiting portion 147 and an anti-slip portion 148 disposed on the external wall of the rotary ring 14.

In addition, the rotary nebulization device 1 of the present invention further comprises a water sealing plate 15 which is a rectangular sheet structure installed outside the liquid storage slot 144 and corresponding to a side of the internal wall of the nebulization ring 13 and tightly coupled to a side of the internal wall of the nebulization ring 13. Further, a side of the water sealing plate 15 has a circular protruding ring 151 with a size corresponding to that of the nebulization module 131.

In addition, the rotary nebulization device 1 of the present invention further comprises a safety ring 16 movably sheathed on the main body 11, the electric connection ring 12, the nebulization ring 13 and the rotary ring 14, wherein the safety ring 16 has a second position-limiting portion 161 and a stop portion 162 disposed on the internal wall of the safety ring 16 and corresponding to the first position-limiting portion 147 and the bump 122 respectively, such that the safety ring 16 can slide outside the main body 11, the electric connection ring 12, the nebulization ring 13 and the rotary ring 14 to prevent the safety ring 16 from falling off.

To improve the convenience of operation, the nebulization ring 13 further has a first indicating portion 136 disposed on the external wall of the nebulization ring 13 and corresponding to the nebulization module, and the rotary ring 14 has a second indicating portion disposed on the external wall of the rotary ring 14 and corresponding to the first indicating portion.

With reference to FIGS. 3 to 6 for the first to fourth schematic views of the using statuses in accordance with a preferred embodiment of the present invention respectively together with FIGS. 1 and 2, the container 2 is installed inside the rotary ring 14 for the use of the rotary nebulization device 1 of the present invention. Now, the safety ring 16 is situated outside the electric connection ring 12, the nebulization ring 13 and the rotary ring 14 to lock the rotary ring 14, and the liquid storage slot 144 and the nebulization module 131 are staggered with each other to define a closed status, and the second contact 142 and the pair of first contacts 121 are also electrically disconnected to avoid the issue of erroneous operations by users. Further, the film breaking structure 145 scratches or cuts the seal film, so that the liquid to be nebulized 21 flows into the liquid storage slot 144, and then the safety ring 16 is moved downwardly to release the locking of the rotary ring 14 and expose the nebulization ring 13. After the rotary ring 14 is rotated till the first indicating portion 135 and the second indicating portion 149 are aligned precisely with each other, the liquid storage slot 144 is also aligned precisely with the nebulization module 131, and thus the liquid to be nebulized 21 flows into the nebulization module 131, and the second contact 142 and the first contact 121 are electric conducted to define an open status, and the liquid to be nebulized 21 can be released, nebulized and sprayed through the nebulization module.

What is claimed is:

1. A rotary nebulization device comprising:

a main body, having a containing space formed therein and provided for installing a power supply;

an electric connection ring, fixed onto a side of the main body and electrically coupled to the power supply, and the electric connection ring having a pair of first contacts disposed thereon;

an nebulization ring, fixed to a side of the electric connection ring, and having an nebulization module interconnected to the outside and electrically coupled to the first contact; and a rotary ring, movably installed onto the nebulization ring, and having a second contact corresponding to the electric connection ring, and an opening portion and a liquid storage slot corresponding to the container, and the opening portion having a film breaking structure corresponding to the seal film, such that when the container is installed to the rotary ring, the film breaking structure scratches or cuts the seal film to let the liquid to be nebulized flow into the liquid storage slot, and the liquid storage slot being normally staggered with the nebulization module to define a closed status, and after the rotary ring is rotated, the liquid storage slot is aligned precisely with the nebulization module, and the second contact and the first contact are electrically conducted to define an open status that releases, nebulizes and sprays the liquid to be nebulized.

2. The rotary nebulization device of claim 1, further comprising a water sealing plate installed on a side of the liquid storage slot corresponding to the internal wall of the nebulization ring and tightly coupled with the internal wall of the nebulization ring.

3. The rotary nebulization device of claim 2, wherein the water sealing plate has a circular protruding ring installed on a side the water sealing plate corresponding to the nebulization module.

4. The rotary nebulization device of claim 3, further comprising an elastic snap-in portion disposed on a side proximate to the liquid storage slot, and the internal wall of the nebulization ring has a position-limiting arc slot corresponding to the elastic snap-in portion, and the elastic snap-in portion is movably snapped into the position-limiting arc slot, such that the rotary ring can be rotated with respect to the nebulization ring within a restricted angular range.

5. The rotary nebulization device of claim 4, wherein the electric connection ring has a snap-in portion disposed on a side of the first contact, and the nebulization ring has a snap-in hole corresponding to the snap-in portion.

6. The rotary nebulization device of claim 5, further comprising a sealing rubber ring installed in the opening portion and disposed at an external periphery of the film breaking structure, and the sealing rubber ring is tightly coupled to an opening of the container.

7. The rotary nebulization device of claim 6, wherein the rotary ring has an anti-slip portion disposed on the external wall of the rotary ring.

8. The rotary nebulization device of claim 7, wherein the nebulization ring has a first indicating portion disposed on an external wall of the nebulization ring corresponding to the nebulization module, and the rotary ring has a second indicating portion disposed on the external wall of the rotary ring corresponding to the first indicating portion.

9. The rotary nebulization device of claim 1, further comprising a safety ring movably sheathed on the exterior of the main body, the electric connection ring, the nebulization ring and the rotary ring.

10. The rotary nebulization device of claim 9, wherein the rotary ring has at least one first position-limiting portion disposed on an external wall of the rotary ring, and the electric connection ring has at least one bump disposed on an external wall of the electric connection ring, and the safety ring has a second position-limiting portion and a stop portion disposed on internal walls of the safety ring corresponding to the first position-limiting portion and the bump respectively for limiting the slide of the safety ring to a position outside the main body, the electric connection ring, the nebulization ring and the rotary ring and preventing the safety ring from falling off.

11. The rotary nebulization device of claim 10, further comprising a water sealing plate installed on a side of the liquid storage slot corresponding to the internal wall of the nebulization ring and tightly coupled with the internal wall of the nebulization ring.

12. The rotary nebulization device of claim 11, wherein the water sealing plate has a circular protruding ring installed on a side the water sealing plate corresponding to the nebulization module.

13. The rotary nebulization device of claim 12, further comprising an elastic snap-in portion disposed on a side proximate to the liquid storage slot, and the internal wall of the nebulization ring has a position-limiting arc slot corresponding to the elastic snap-in portion, and the elastic snap-in portion is movably snapped into the position-limiting arc slot, such that the rotary ring can be rotated with respect to the nebulization ring within a restricted angular range.

14. The rotary nebulization device of claim 13, wherein the electric connection ring has a snap-in portion disposed on a side of the first contact, and the nebulization ring has a snap-in hole corresponding to the snap-in portion.

15. The rotary nebulization device of claim 14, further comprising a sealing rubber ring installed in the opening portion and disposed at an external periphery of the film breaking structure, and the sealing rubber ring is tightly coupled to an opening of the container.

16. The rotary nebulization device of claim 15, wherein the rotary ring has an anti-slip portion disposed on the external wall of the rotary ring.

17. The rotary nebulization device of claim 16, wherein the nebulization ring has a first indicating portion disposed on an external wall of the nebulization ring corresponding to the nebulization module, and the rotary ring has a second indicating portion disposed on the external wall of the rotary ring corresponding to the first indicating portion.

* * * * *